United States Patent
Metzger et al.

(10) Patent No.: US 11,331,251 B2
(45) Date of Patent: May 17, 2022

(54) METHOD AND SYSTEM FOR SELECTIVE HAIR BRIGHTENING

(71) Applicant: XTREAMHAIR LTD., Netanya (IL)

(72) Inventors: David Metzger, Natanya (IL); Avraham Stern, Netanya (IL)

(73) Assignee: XTREAMHAIR LTD., Netanya (IL)

( * ) Notice: Subject to any disclaimer, the term of this patent is extended or adjusted under 35 U.S.C. 154(b) by 0 days.

(21) Appl. No.: 16/968,023

(22) PCT Filed: Feb. 28, 2019

(86) PCT No.: PCT/IB2019/051616
§ 371 (c)(1),
(2) Date: Aug. 6, 2020

(87) PCT Pub. No.: WO2019/166983
PCT Pub. Date: Sep. 6, 2019

(65) Prior Publication Data
US 2021/0030643 A1    Feb. 4, 2021

Related U.S. Application Data

(60) Provisional application No. 62/636,865, filed on Mar. 1, 2018.

(51) Int. Cl.
| | |
|---|---|
| *A61K 8/22* | (2006.01) |
| *A61K 8/9794* | (2017.01) |
| *A61K 8/9789* | (2017.01) |
| *A45D 19/00* | (2006.01) |
| *A45D 7/04* | (2006.01) |
| *A45D 19/18* | (2006.01) |

(Continued)

(52) U.S. Cl.
CPC .................. *A61K 8/22* (2013.01); *A45D 7/04* (2013.01); *A45D 19/012* (2021.01); *A45D 19/18* (2013.01); *A45D 44/005* (2013.01); *A45D 44/02* (2013.01); *A61K 8/342* (2013.01); *A61K 8/362* (2013.01); *A61K 8/416* (2013.01); *A61K 8/4926* (2013.01); *A61K 8/9789* (2017.08); *A61K 8/9794* (2017.08); *A61Q 5/08* (2013.01); *A45D 19/0075* (2021.01); *A45D 2044/007* (2013.01)

(58) Field of Classification Search
CPC . A61Q 5/08; A61K 8/22; A61K 8/342; A61K 8/362; A61K 8/4926; A61K 8/416; A45D 19/0066; A45D 2200/205; A45D 44/005; A45D 44/04; A45D 19/18; A45D 44/02; A45D 7/04; A45D 19/0075; A45D 2044/007
USPC .............................................. 424/62; 132/208
See application file for complete search history.

(56) References Cited

U.S. PATENT DOCUMENTS

| | | | |
|---|---|---|---|
| 6,312,675 B1 | 11/2001 | Deane | |
| 6,814,762 B2 * | 11/2004 | Matsunaga | ............ A61Q 5/065 132/208 |

(Continued)

FOREIGN PATENT DOCUMENTS

DE     102016009273     2/2018

*Primary Examiner* — Eisa B Elhilo
(74) *Attorney, Agent, or Firm* — Reches Patents

(57) ABSTRACT

A system, computer readable medium and method for selective brightening of hair, the method may include or may be preceded by applying at least one photosensitive material to the hair. The method may also include forming at least one pattern of brightened hair by illuminating the hair by at least one pattern of illumination.

27 Claims, 19 Drawing Sheets

(51) Int. Cl.
        *A45D 44/00*      (2006.01)
        *A45D 44/02*      (2006.01)
        *A61K 8/34*       (2006.01)
        *A61K 8/362*      (2006.01)
        *A61K 8/41*       (2006.01)
        *A61K 8/49*       (2006.01)
        *A61Q 5/08*       (2006.01)

(56) References Cited

U.S. PATENT DOCUMENTS

| | | | |
|---|---|---|---|
| 9,693,937 B2 * | 7/2017 | Kleen | A61K 8/4966 |
| 2007/0167936 A1 * | 7/2007 | Samain | A45D 19/00 |
| | | | 606/9 |
| 2015/0224041 A1 * | 8/2015 | Greaves | A61Q 5/10 |
| | | | 132/208 |
| 2017/0013943 A1 | 1/2017 | Uchida | |
| 2017/0042776 A1 | 2/2017 | L'Oreal | |

* cited by examiner

302

METHOD AND SYSTEM FOR SELECTIVE HAIR BRIGHTENING

CROSS REFERENCE

This application claims priority from U.S. provisional patent 62/636,865 filing date Mar. 1, 2018 which is incorporated herein by reference.

BACKGROUND

Selective bleaching of hair is very common, and it is claimed that every third woman in the western world undergoes this procedure at least two times a year. The current procedure is relatively long in duration, costly, not well controlled, and uses harmful bleaching materials to produce brightening/bleaching of the hair. It typically includes grouping of the hair into multiple clusters, applying to each cluster the bleaching material, wrapping each cluster with aluminum foil, waiting for about one-two hours, and finally taking off the foils and rinsing the hair. The actual brightening occurs due to the chemical reaction of the bleaching material, and occurs only where the material was applied. The procedure is not well controlled, and highly depends on the hairdresser's expertise.

Apart from the complex and time-consuming procedure, currently, there is no possibility to bleach specific patterns or shapes on the hair, for example horizontal lines, triangles, letters, etc.

SUMMARY

Any combination of each step of any method illustrated in the application may be provided. The subject matter of each one of the originally method claims may be combined. Any combination of any system components may be provided.

There may be provided a system that may include a holding element for holding hair; and pattern forming elements that may be configured to form at least one pattern of brightened hair by illuminating at least one photosensitive material applied to the hair by at least one pattern of illumination. The pattern forming elements may include one or more radiation sources, one or more masks, and one or more other optical elements.

The system may be configured to form the at least one pattern may include illuminating a mask positioned between a radiation source and the hair to provide the pattern of illumination.

The illuminating may be preceded by positioning the hair between the mask and a holding element element.

At least one of the mask and the radiation source may be proximate to a back of a seat.

The mask may be a fixed mask.
The mask may be a configurable mask.
The mask may be a planar mask.
The mask may be a three dimensional mask.

The pattern forming elements may include a scanner that may be configured to scan at least one radiation beam to provide the at least one pattern of brightened hair.

The pattern forming elements may include multiple radiation sources that may be configured to form the at least one pattern by illuminating the hair from multiple directions.

The pattern forming elements may include multiple independently controllable radiation sources that may be configured to form the at least one pattern by illuminating the hair from multiple directions.

The pattern forming elements may include a helmet that may include at least one illumination source that may be configured to form the at least one pattern by illuminating the hair from multiple directions.

The system may be configured to form the at least one pattern by forming a pattern of nonuniform brightness.

The system may be configured to form the at least one pattern by forming a pattern of a uniform brightness.

The radiation may have a wavelength that ranges between 365 and 435 nanometer.

The radiation may have a wavelength that ranges between 400 and 435 nanometer.

The radiation may have a power density that does not exceeds Watt/cm.

The system may include a monitor that may be configured to monitor the hair and determine when to stop the illuminating based on a result of the monitoring.

The pattern forming elements may include one or more light emitting diodes.

The pattern forming elements may include one or more ultraviolet lamps that may be configured to illuminate the hair from multiple directions.

The pattern forming elements may include one or more blue lamps that may be configured to illuminate the hair from multiple directions.

The system may be configured to inspect the hair before the forming of the at least one pattern; and when a controller of the system may be configured to determine at least one illumination parameter based on an outcome of the inspecting and one or more properties of the at least one pattern.

There may be provided a computer readable medium that stores instructions for receiving hair that may include at least one photosensitive material; and forming at least one pattern of brightened hair by illuminating the hair by at least one pattern of illumination.

BRIEF DESCRIPTION OF THE DRAWINGS

In order to understand the invention and to see how it may be carried out in practice, a preferred embodiment will now be described, by way of non-limiting example only, with reference to the accompanying drawings.

DETAILED DESCRIPTION OF THE DRAWINGS

Figure 1:
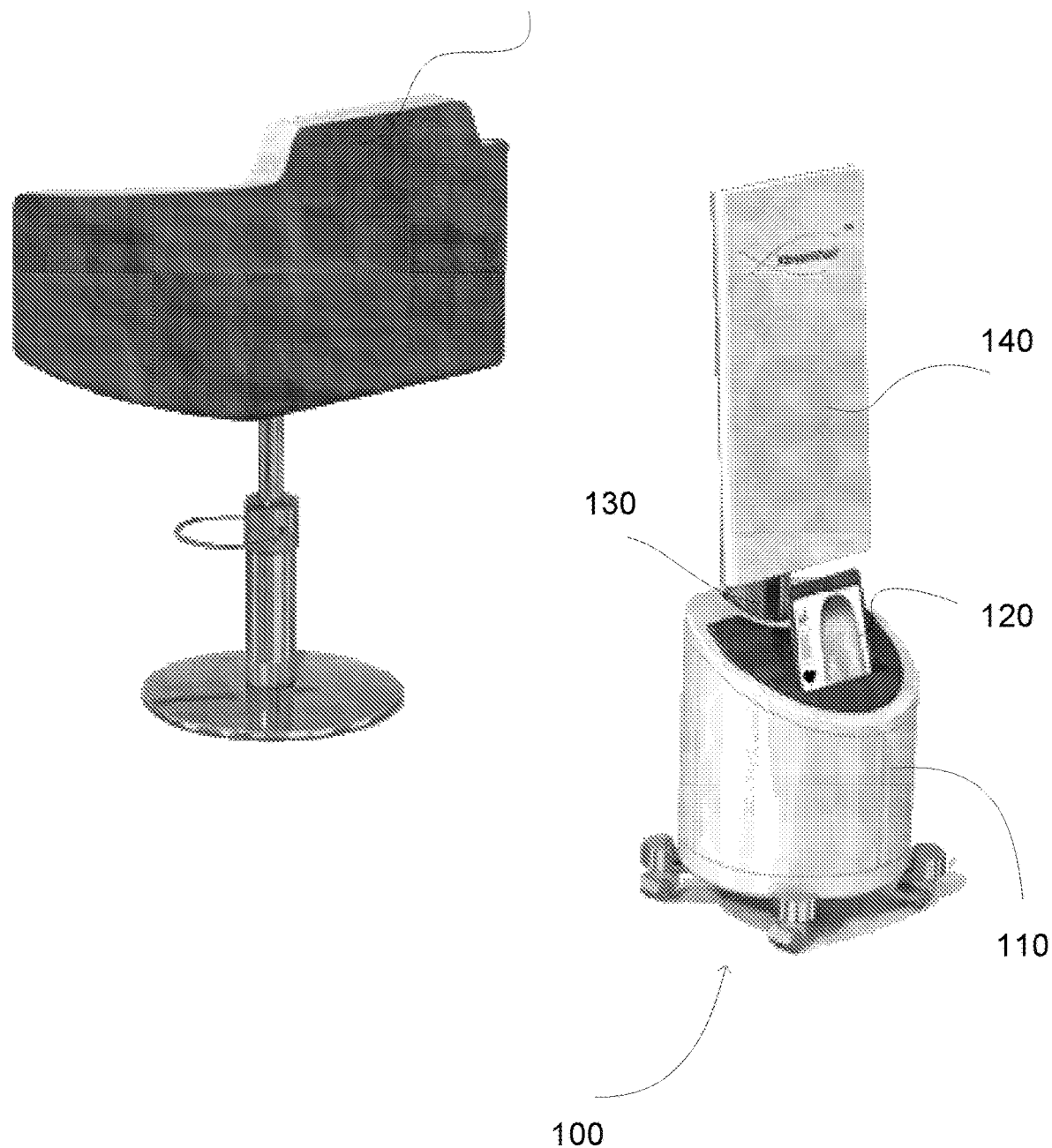
FIG. 1 is an example of a system and a chair.

Here we propose a method, a system and a computer program product for selectively brightening hair—to provide patterns—in a fast and controlled manner. The method is based on photosensitive materials which are applied to the hair, and when they are exposed to light the hair undergoes brightening. Any brightening pattern may be obtained by controlling the illumination of the hair.

The hair (or rather selected parts of the hair) may be illuminated by radiation. The radiation may be provided from one or more radiation sources. The radiation sources may be followed by one or more optical elements (such as lenses, polarizers, beam splitters, lightguides and the like) but for simplicity of explanation most of the figures and text do not illustrate these optical elements. Thus—any reference to a radiation source may also be regarded to a reference to the combination of a radiation source and the one or more optical elements).

A shape of the brightening pattern may be defined by a mask positioned between a light source and the hair. The mask may be a fixed mask or a configurable mask (for example an LCD or other spatial light modulator mask). Additionally or alternatively, the shape of the brightening pattern may be obtained by using multiple independently controllable light sources—without a mask. Yet a combination of a mask (or more than a single mask) and more than one radiation source may be provided.

The amount of brightening throughout the brightening pattern may be uniform or ununiform. The brightening at each point of the brightening pattern may be determined by the intensity of illumination. The intensity of illumination may be uniform or ununiform. The intensity may be determined by using masks of controllable transparency, by controlling the intensity distribution of one or more light sources, by controlling the exposure times at one or more different points of the pattern, and the like.

Additionally or alternatively, the brightness may be affected by the photosensitive materials—and by the distribution of the photosensitive materials over the hair.

The actual brightening depends on the exposure time and on the light power density. If the material is applied to a large section of the hair and the light is shined through a mask, various patterns and shapes can be obtained. The system may include an illumination unit, one or more sensors and a controller.

The illumination unit may include one or more light sources, the one or more sensors may be used for monitoring the progress of the brightening process. In the following pages various examples of these elements are used. These example (as any other example illustrated in the application) are merely non-limiting examples.

The one or more sensors may be light sensors, heat sensors, and the like.

The system may include holding elements for holding the hair while the hair is illuminated—especially for maintaining a known spatial relationship between the hair and the illumination unit.

The system may include several submodules—the high brightness LED array source unit, the power supply unit, sensor elements, and the controller.

With this concept it is possible to accomplish any desired brightening pattern—such as but not limited to selective hair shades/highlights, "Ombre" (bleaching of the lower part of the hair), special patterns.

The Light Source

The light source may include an array of LEDs at wavelengths between 365-430 nm. Other wavelengths may be used. Within this wavelength region it is beneficial to use light with wavelengths longer than 400 nm in order to avoid skin exposure to UV light. According to our preliminary experiments the power densities required for the bleaching are up to 2 W/cm$^2$. The LED array can be of various shapes and sizes (a uniform plate, in a helmet shape, or locally arranged; see system description).

The light source can also be realized with a laser source in the above wavelength region and similar power densities. If the laser beam size is small relative to the desired pattern, a scanning mechanism that will scan the beam across the hair will be needed.

The light source can also be realized with a special projector that illuminates a pattern on the hair at the above wavelengths. The projector can be based on either a UV/blue lamp or on a suitable laser or LED array.

The Chemical Materials

The possible photosensitive chemical compounds may be based on at least some of the following ingredients:

Water, Hydrogen Peroxide, Cetyl Alcohol (emulsifier and thickening agent), Behentrimonium chloride (an antistatic agent and conditioner), polyquatemium 10 (increasing hair body), panthenol (a moisturizer and to improve healing), *Aloe vera* extract, *Camellia sinesis*, isopropyl myristate (enhance the penetration), niacinamid (part of the vitamin B group), fragrance, citric acid, geraniol (a rose oil).

Possible additives can be:

Paraoxide materials, natural polar materials, plant extracts, and gold or silver nanoparticles to enhance the photosensitivity.

There may be provided a composition of materials ("composition) that allows for less than 5 minutes hair brightening.

The composition may include substances that may include one or more hydrogen radicals that may whiten the hair with additives of surfactants, natural plant extracts, lubricants materials that are designed to whiten the hair and give it shine and vitality.

For example—the composition may include at least a majority of the following substances—the table illustrated examples (A-F) of percentages—although the percentages in the composition may change from those illustrated in the table below:

|  | A | B | C | D | E | F |
| --- | --- | --- | --- | --- | --- | --- |
| Acetone Peroxide | 0.1000 | 0.3000 | 0.6000 | 0.5000 | 0.4000 | 0.8000 |
| Alcohol | 11.0000 | 15.0000 | 20.0000 | 25.0000 | 0.0000 | 0.0000 |
| Benzoic acide | 0.0000 | 0.1000 | 0.0600 | 0.0400 | 0.0300 | 0.0400 |
| Benzophenone | 0.0000 | 0.0000 | 0.5000 | 0.9660 | 0.0000 | 0.8155 |
| Benzoyl Peroxide | 0.0000 | 0.1000 | 0.0300 | 0.0078 | 1.0000 | 0.5000 |
| Benzyl | 0.0560 | 0.0000 | 0.0000 | 0.0000 | 0.0000 | 0.0000 |
| Benzylbenzoic acid | 0.1000 | 0.0000 | 0.0000 | 0.0000 | 0.0000 | 0.0000 |

-continued

|  | A | B | C | D | E | F |
|---|---|---|---|---|---|---|
| Calcium peroxide | 0.0000 | 0.0100 | 0.0120 | 0.0300 | 0.0000 | 0.0000 |
| *Calendula officinalis* flowe | 0.0100 | 0.4960 | 0.0100 | 0.0100 | 0.0100 | 0.0100 |
| *Chamomilla recutita* (*matricario*) flower extract | 0.0100 | 0.0100 | 0.0100 | 0.0100 | 0.0100 | 0.0100 |
| Chlorine | 0.0000 | 0.0500 | 0.1000 | 0.2000 | 0.3000 | 0.4000 |
| Dimethicone peg-7 phosphate | 0.0050 | 0.0050 | 0.0050 | 0.0050 | 0.0050 | 0.0050 |
| Disodium edta (235-228) | 0.0200 | 0.0200 | 0.0200 | 0.0200 | 0.0200 | 0.0200 |
| Fragrance | 0.0050 | 0.0050 | 0.0050 | 0.0050 | 0.0050 | 0.0050 |
| Glycerin | 6.0000 | 6.0000 | 3.7839 | 0.7820 | 5.0000 | 3.0000 |
| Guar Gum | 0.2000 | 0.2000 | 0.2000 | 0.2000 | 0.2000 | 0.2000 |
| Hydrogen peroxide(30%) | 20.0000 | 20.0000 | 20.0000 | 25.0000 | 30.0000 | 34.0000 |
| Hydroxyethyl cetyldimonium phosphate | 0.0500 | 0.0500 | 0.0500 | 0.0500 | 0.0500 | 0.0500 |
| *Linumusitatissimum* (linseed) seed extract | 0.0500 | 0.0500 | 0.0500 | 0.0500 | 0.0500 | 0.0500 |
| Nano Cooper powder | 0.0000 | 0.0000 | 0.0001 | 0.0002 | 0.0004 | 0.0005 |
| Nano Silver powder | 0.0100 | 0.0200 | 0.0300 | 0.0400 | 0.0500 | 0.0000 |
| Oleo *barbadensis* leaf juice | 0.0010 | 0.0010 | 0.0010 | 0.0010 | 0.0010 | 0.0010 |
| Panthenol | 2.0000 | 1.5000 | 1.0000 | 2.0000 | 2.7856 | 0.0100 |
| Polysorbate 20 | 0.0500 | 0.0500 | 0.5000 | 0.0500 | 0.0500 | 0.0500 |
| Quaternium - 80 | 0.0300 | 0.0300 | 0.0300 | 0.0300 | 0.0300 | 0.0300 |
| Silk amino acid | 0.0030 | 0.0030 | 0.0030 | 0.0030 | 0.0030 | 0.0030 |
| Water | 60.0000 | 56.0000 | 53.0000 | 45.0000 | 60.0000 | 60.0000 |
| xanthan Gum | 0.3000 | 0.3000 | 0.3000 | 0.3000 | 0.3000 | 0.3000 |
|  | 100.0000 | 100.0000 | 100.0000 | 100.0000 | 100.0000 | 100.0000 |

The composition may be included in a liquid or in a gel.

Yet for another example—the composition may include at least the following components:

a. Free Peroxide—Agent for bleaching hair under the influence of light to be used according to the above-described method in the form of a solution or emulsion containing a least one compound which is capable of providing a hydrogen radical, characterized in that it is free of peroxides and contains at least one optical photosensitizer like: Hydrogen peroxide, benzoyl peroxide Benzophenone, benzyl, benzyl benzoic acid.

b. Silver and copper nanoparticles—These particles help get the energy from the radiation and transfer it to the environment to help extract the peroxides c. Stabilizers and emulsifiers—Ensure that the emulsion is homogenous and stable, that all particles are equally distributed in emulsion.

d. Extraction of plants—to reducing inflammations and expediting the healing of wounds, it's also been shown to cure fungal disorders. It has a powerful skin regeneration, shining and anti-aging ingredient.

e. Surfactants—As antistatic agent and hair conditioning agent.

f. Water—forms the remainder of the composition. It is generally present at a level of from about 40% to about 60%.

There is provided an example for manufacturing the composition. Other methods of manufacture can be used.

a. Step One—pre-mix the nanoparticles with suspension through a high shear mill to create better dispersion and homogeneity.

b. Step two—mix all the stabilizers and the emulsifier's in water while heating to 85 degrees.

c. Step three—cool the mass through a heat exchanger to reach a room temperature.

d. Step four—mix the rest of the ingredients with a homogenizer, and achieve uniformity.

e. Step five—fill the product with the packages designated for it.

The System

FIG. 1 illustrates a system and a chair 20. The chair may not be a part of the system 100.

Figure 2:
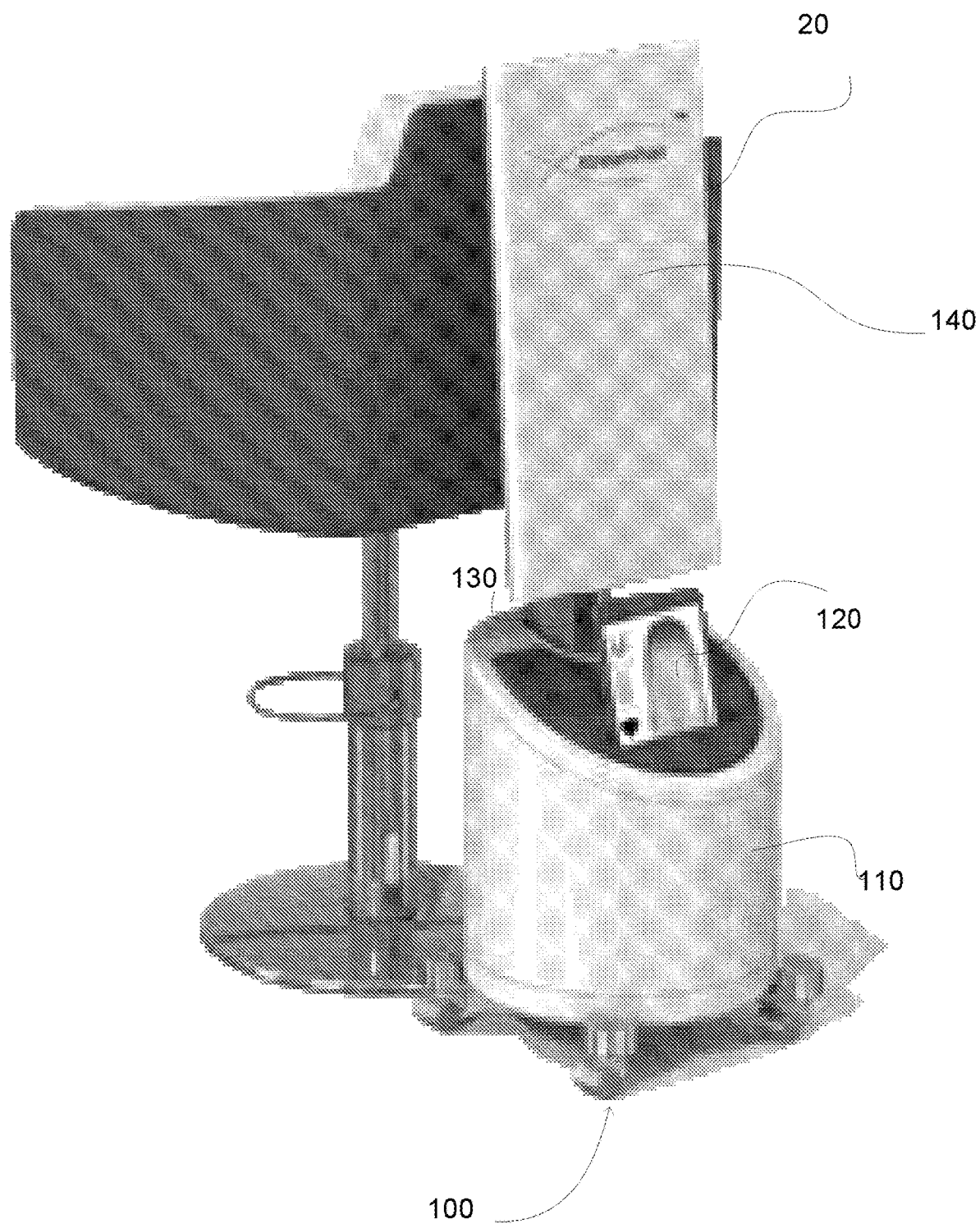
FIG. 2 is an example of a system and a chair.
Figure 3:
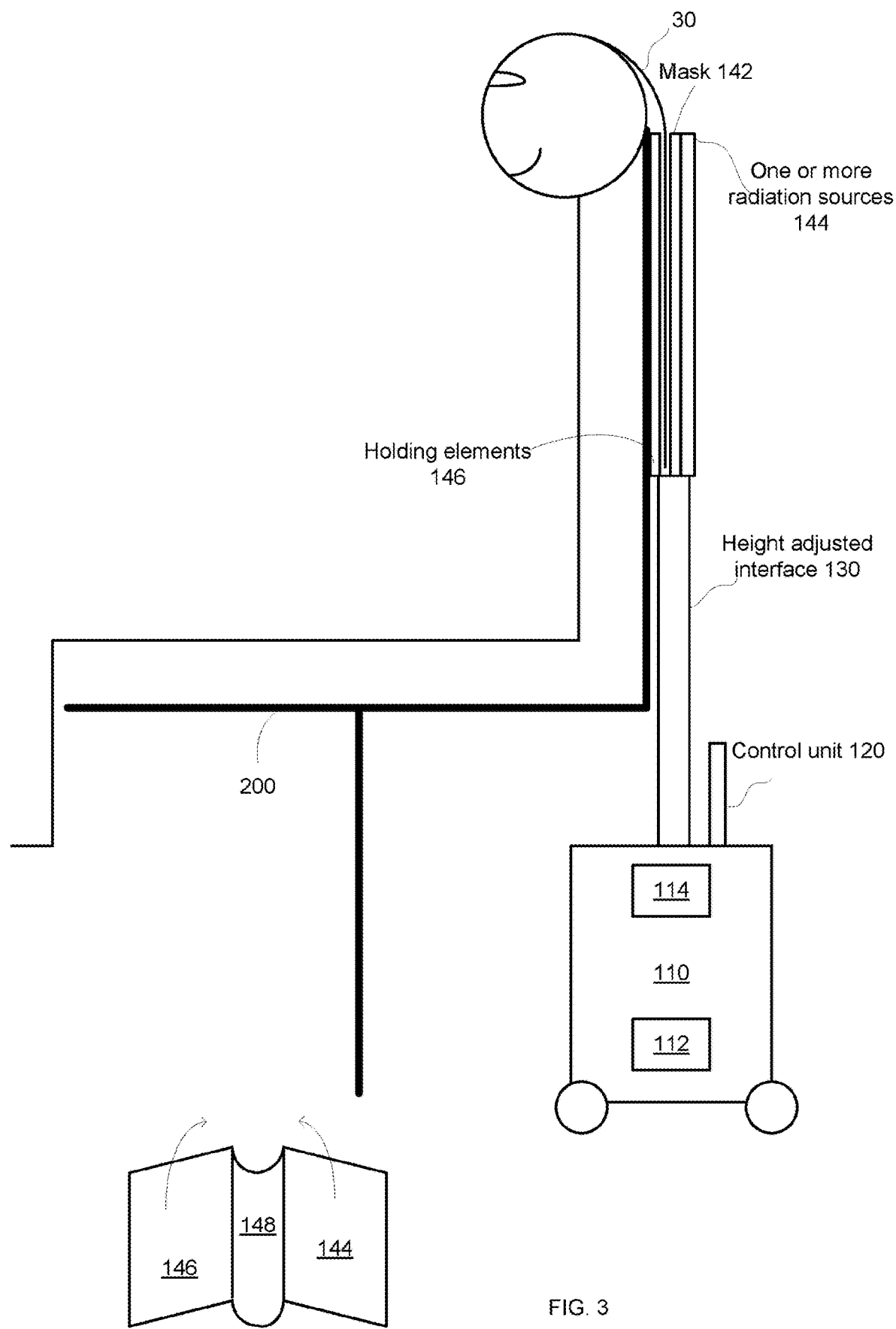
FIG. 3 is an example of a system and a chair.

FIGS. 1-3 illustrates a "plate" configuration for selective brightening in the lower part of the hair. The plate refers to the fact that the mask and radiation sources are located in a top part 140 that is substantially planar.

The top part 140 may include a mask 142 and one or more radiation sources 144 (such as but not limited to an LED array in a form of a plate).

The top part may also include a holding element 146. The holding element may be static and the mask and the one or more radiation sources may move in relation to the holding element. The hair can be held between the holding element 146 and the mask 142. The hair may be positioned between the mask 142 and the holding element (when the top part is at an open position) and then firmly held—or otherwise sandwiched between the mask and the holding element. The holding element may be fastened to the mask—or held in any other manner during the illumination of the hair. FIG. 3 illustrated a flexible connector 148 for connecting the mask to the holding element. The connector may include axes over which the mask and/or the holding element may rotate- and may not be flexible.

The top part 140 is mechanically coupled to a height adjustment interface 130—such as a rod, a pole, that is configured to elevate or lower the top part in relation to the main body 110 of the system.

The system may have a shape that resembles a trolley—the main body is supported by wheels and can be easily moved from one place to another.

The part of the hair that should be bleached is positioned between the mask and the holding element. Radiation from the one or more radiation sources may pass through the mask and selectively brighten the hair to provide one or more patterns.

It should be noted that trolley shape is merely an example of a movable system. The system may have any shape and/or size and/or configuration that allows it to illuminate hair in a desired matter to obtain the desired pattern.

It should be noted that the hear may be illuminated from the outside and from the inside. For example one or more radiations sources and/or a mask may be positioned in FIG. 1-3 in the side of the supporting element.

Figure 4:
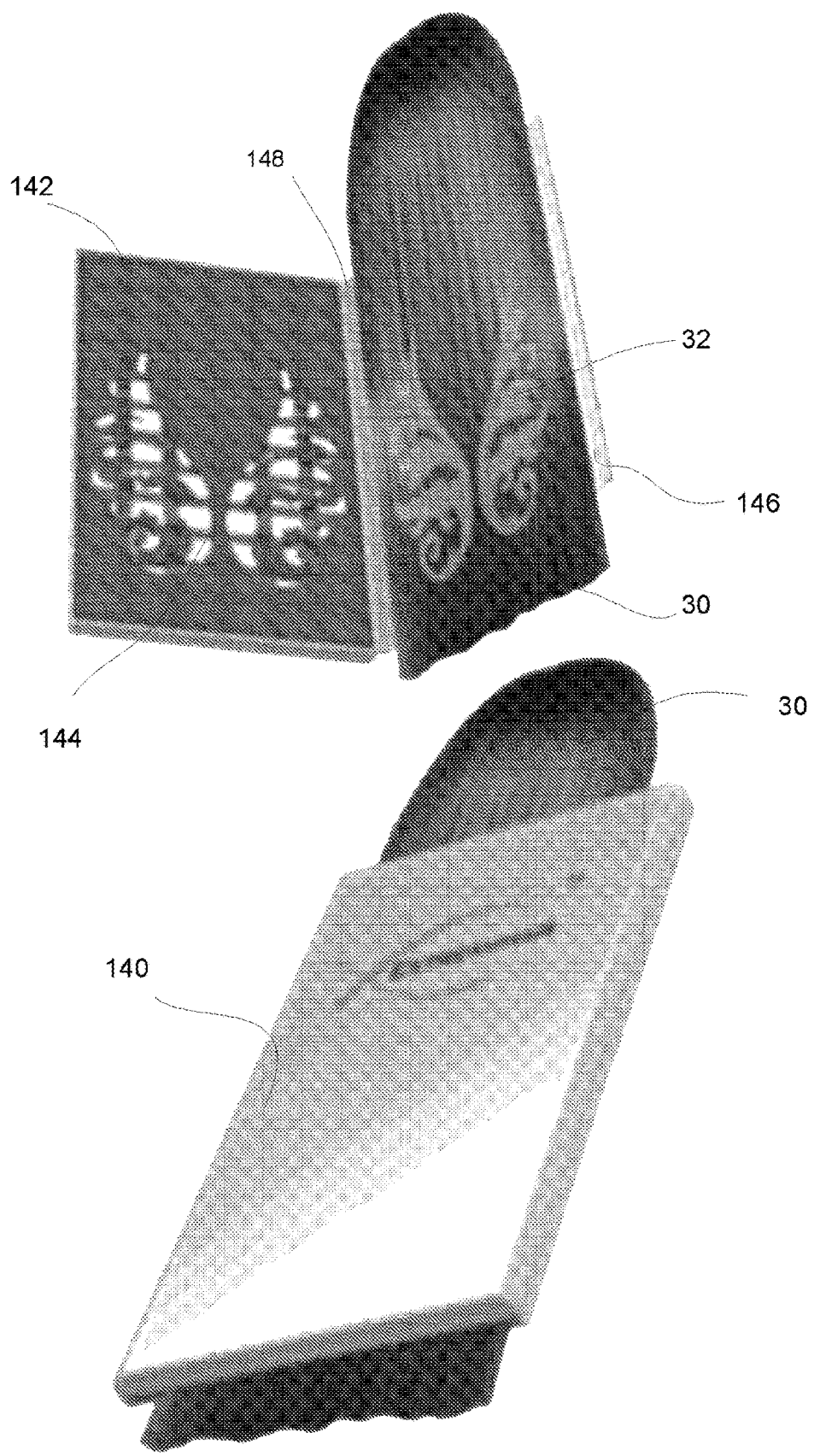
FIG. 4 is an example of hair, a mask and a holding element.

FIG. 4 illustrates that the one or more radiation sources (LED array) are mounted on one side of the plate, and shines the light through a replaceable mask 144 that transmits light in a specific desired pattern.

Referring back to FIG. 3—the LED plate may be cooled with water (provided from a water supply—chiller), the chiller 112 may be positioned within the main body 110. The main body may also include various electronics and/or components to drive the LED's (for example by controller 114). The whole system may be controller by a control unit 120. The control unit 120 may not belong to the system—but may be computer/tablet/mobile phone or similar.

Figure 5:
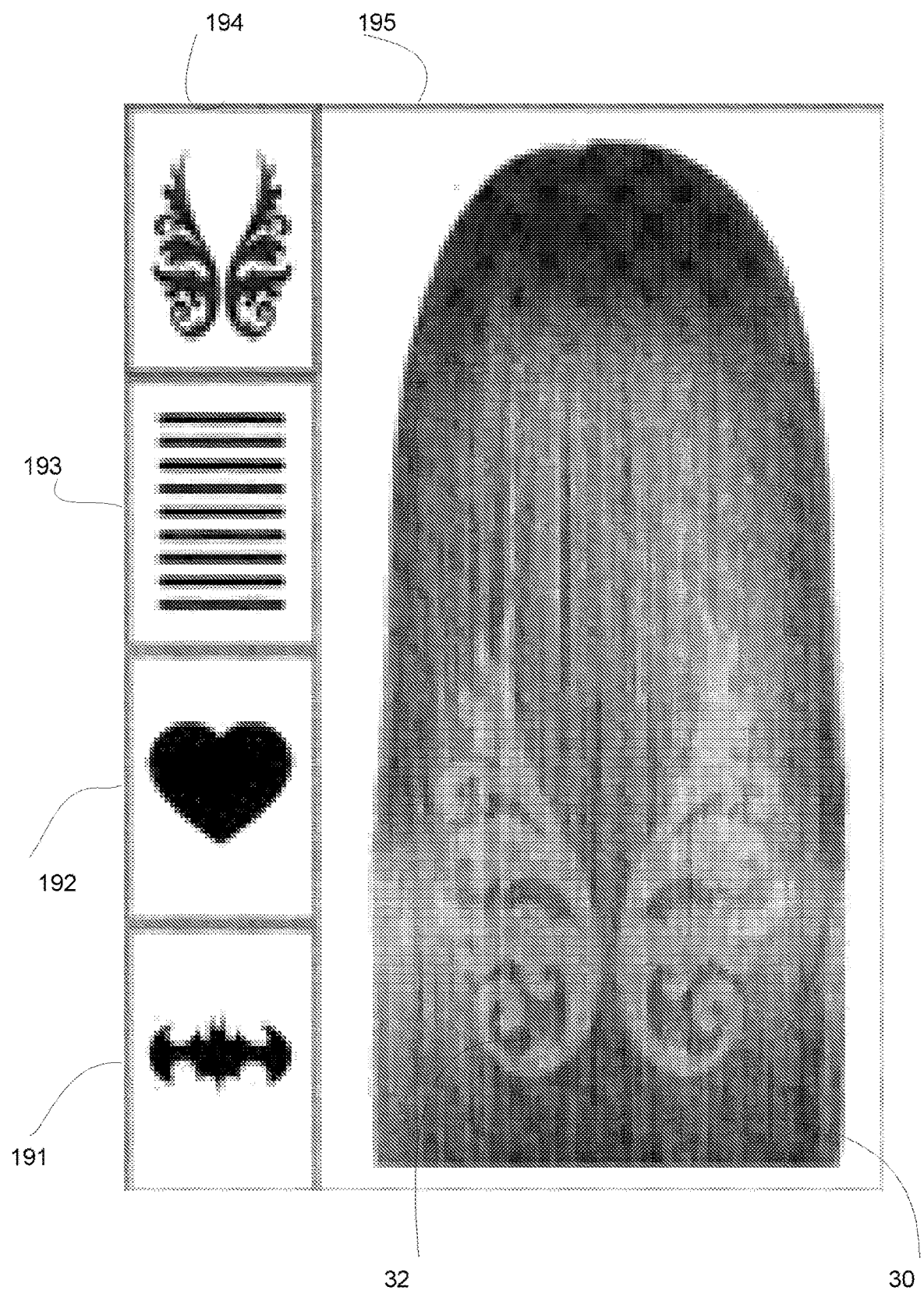
FIG. 5 is an example of a display.

FIG. 5 illustrates an interface 190 that may display (in different windows 191, 192, 193 and 194) different patterns to be formed on the hair, and may display 195 an expected outcome of the selective brightening process—a pattern 32 formed on the hair.

Figure 6:
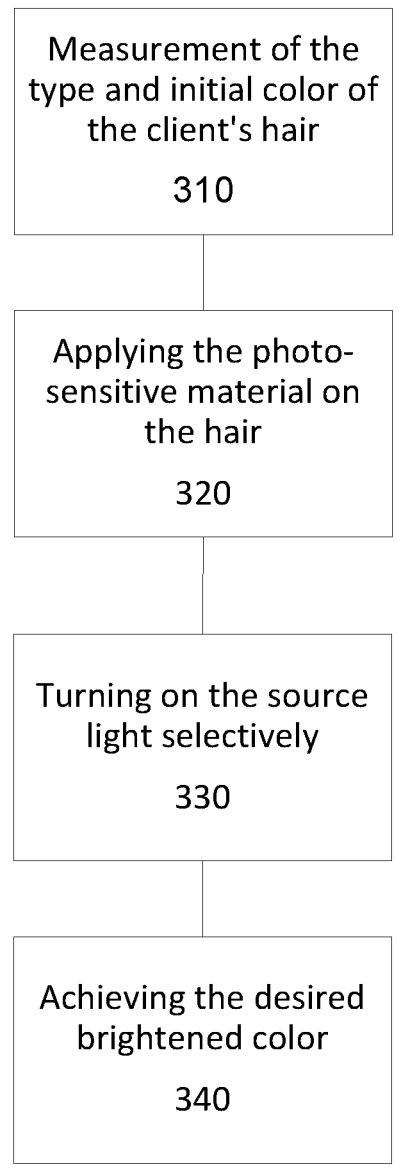
FIG. 6 is an example of a selective brightening process.

FIG. 6 illustrates an example of a procedure of the selective brightening—measuring (310) the hair (type and initial color), applying (320) a photosensitive material to the hair (by spraying, rinsing, brush, etc., using the system 100 or using non-system components or means), then there is a dwell period (for example—up to 20 minutes) in which the material penetrates the hair, then the plate is closed on the hair (see FIG. 3), and then illuminating the hair (330) through a specific mask (for example—up to 10 minutes), monitoring the process and stopping the illumination when achieving the desired brightened color (340).

In step 310 the operator measures the color and type of hair, and this is fed into the system 100. The client may chooses the desired brightening color (shade or shades), and this is also fed into the system. The system is pre-calibrated, and determines the amount of time and the power density level that will be used in the procedure.

Instead of the static masks that are put in front of the LED array, it is also possible to not use a mask, and turn on specific LED's in the array, thus achieving selective brightening and specific patterns on the hair. The brightening may be controlled (adjusting illumination parameters such as frequency, intensity, angle of illumination) based on a pre-defined mapping and/or may also be based on feedback provided during the brightening process. A monitor may perform the monitoring and may include one or more sensors for sensing the progress of the brightening and a controller for controlling the process based on the requested brightening and the actual brightening.

In another example—there may be provided a "helmet" concept for selective brightening in upper part of the hair (close to the head).

Figure 7:
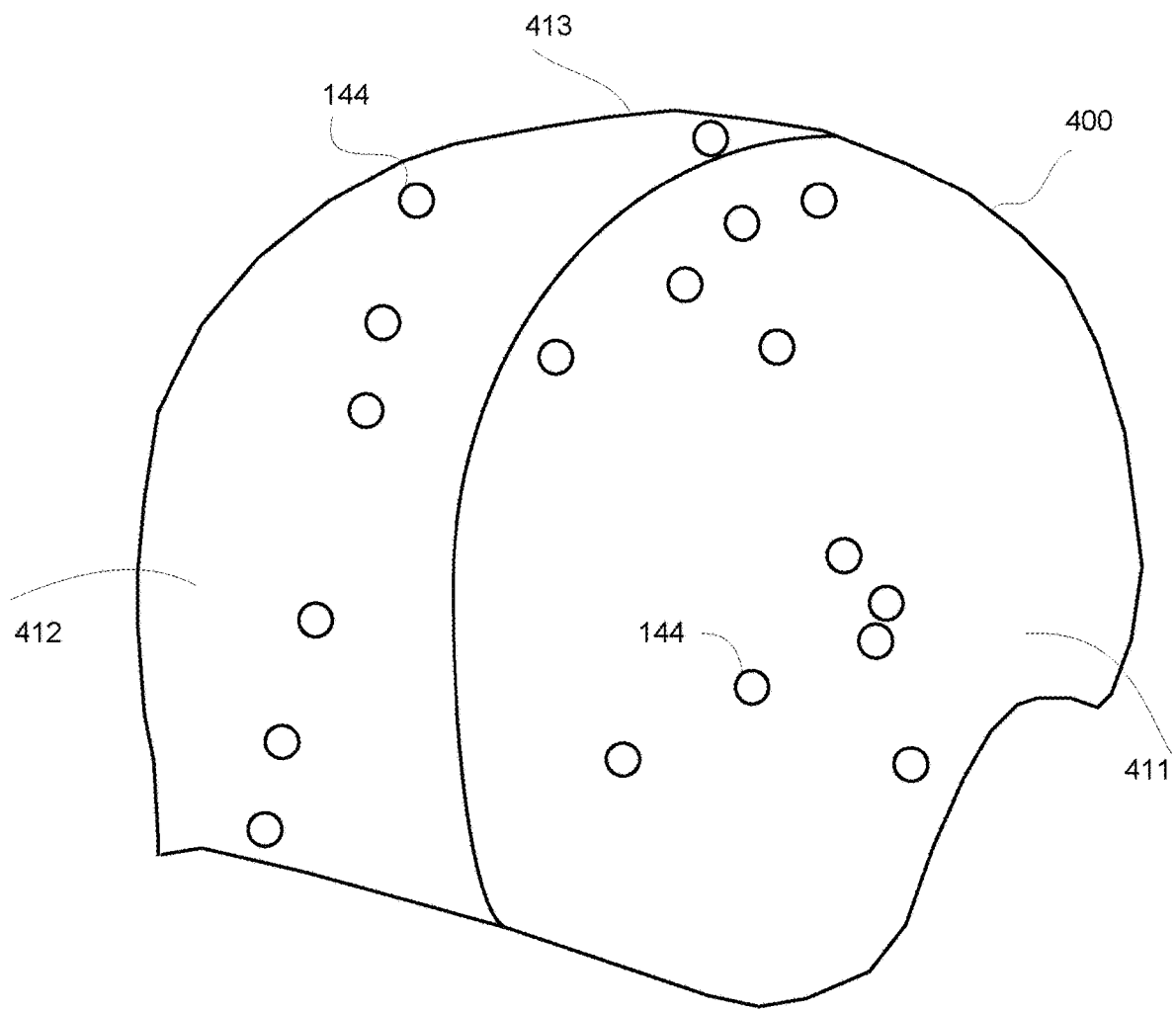
FIG. 7 is an example of a helmet.

Here, the LED array 144 or other radiation sources are mounted in a helmet (see helmet 400 of FIG. 7) that will be worn by the client. As in the plate concept, there may be masks within the helmet, or selective operation of the radiation sources in the helmet array, in order to achieve selective illumination of the hair.

Figure 8:
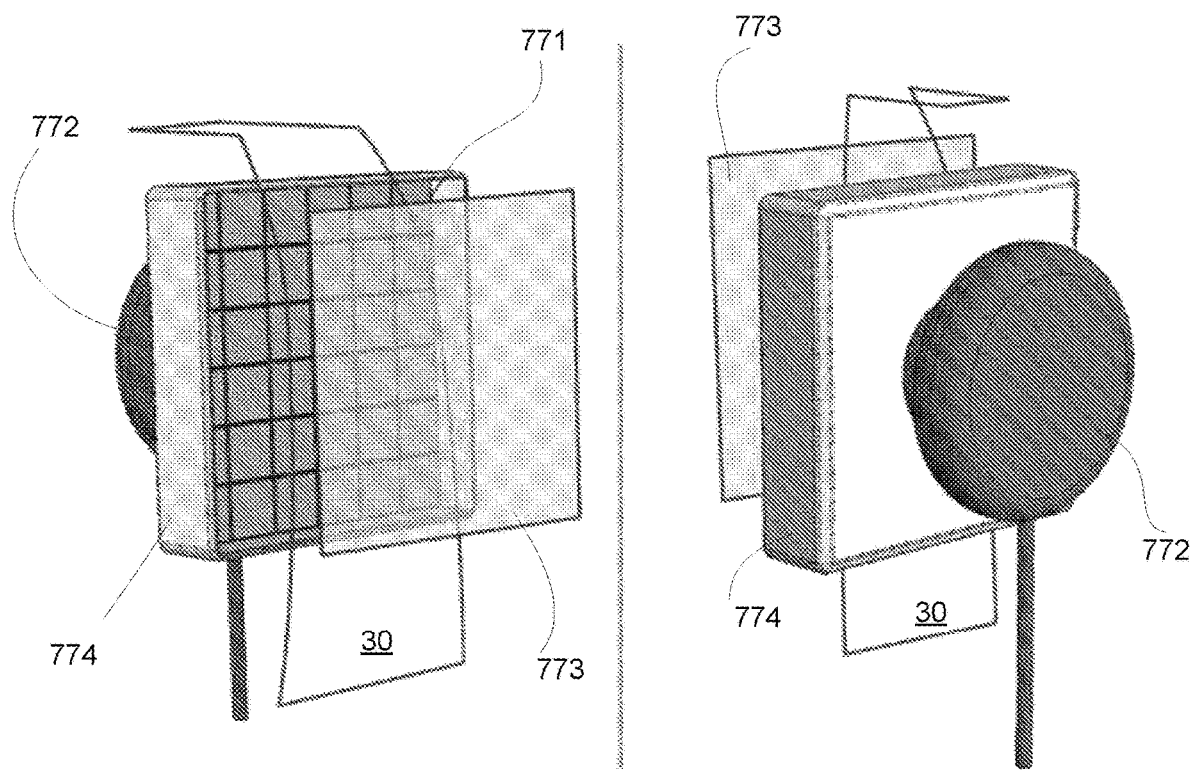
FIG. 8 illustrates an example of an illumination unit.

FIG. 8 illustrates an illumination unit 770 of the system. The illumination unit 770 can be moved (by a human or aby a machine) in relation to the hair 30—when generating the at least one pattern. The illumination unit 770 may include a handle 772 for holding a housing 774 of the illumination unit, wherein radiation sources (such as an array of radiation sources 771 are included in the housing—thus allowing manual movement during the brightening process—in order to brighten one part of a pattern after the other. If the LED's illumination is patterned (e.g. in a periodic manner), then the resulting hair will be brightened in a corresponding pattern.

Figure 9:
FIG. 9 is an example of a system that has a scanning laser.

In a further example—the system may use scanning laser for hair brightening. FIG. 9 illustrates a system with a scanning laser 181. The laser is include din an optical head 181 that can scan the laser—mechanically and/or optically.

Here a laser beam illuminates the hair from a distance. Because the footprint of the laser beam on the hair is small, a scanning mechanism is required. This can be two mirrors that scan in perpendicular axis, or other type of deflectors. The laser can "draw" different shapes and patterns on the hair, and since the whole hair has the photosensitive material, wherever the beam hits it will activate the photosensitive reaction and will brighten the hair. It is possible also to use diffractive optical elements in front of the laser beam to further structure the illumination patterns on the hair.

The scanning laser may be replaced by any scanning light source and/or any optics that may scan a light beam over the hair according to a desired pattern.

The Projector Concept for Hair Brightening

Here, a high brightness projector is used to image a pattern on the hair at the required wavelengths (365-430 nm). The projector light source can be a strong UV lamp, or powerful LEDs, or laser, etc. The picture can be generated by LCD or other type of display that can change the phase/amplitude/color in an addressable manner (i.e. for each pixel). This picture is then imaged by an optical system on the hair.

The Hair Color Sensor

The system may have an integrated hair color sensor that will measure the color of the hair one or multiple times during the process—thereby allowing the system to stop the process once a desired color is obtained. These measurements will help control the brightening process in an automatic manner. The color sensor can be based on a variety of mechanisms, including silicon CCD camera's/chips, CMOS sensors, etc. Controlled separate external lighting may be used when measuring the hair color, in order to achieve repeatable results that are independent (as much as possible) from the ambient lighting in the room.

The system may determine in any manner how to perform the brightening process and when to stop it—based on the readings of the one or more sensors. For example—the system may include lookup tables that will be used to decide the illumination power density level and the exposure time. Alternatively—the system may use a formula or other function to determine the parameters of the brightening process. The optimal illumination may not be constant in time, but may have a specific power illumination curve (e.g. in the beginning high and then decrease, or in the beginning low and then increase, etc.).

The system may allow data recording, in order to obtain statistics and data for optimizing the procedure. It may save data of specific customers for use in their next visit. It may be used for better classification of types of hair, etc. The system may be an adaptable "learning" system.

The sensor may be used also for online monitoring of the process, in order to determine the power density and illumination in a real-time manner (on-the-fly).

Preliminary Results

Figure 10:
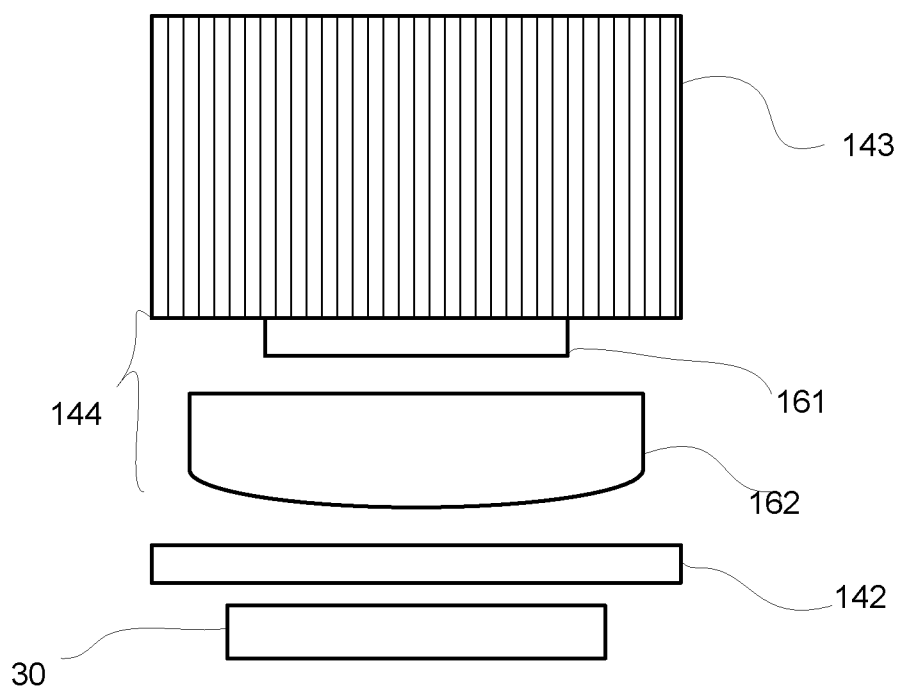
FIG. 10 is an example of an experimental setup.

In the preliminary experiments the inventors tested brightening of hair of different types with several photosensitive compounds, different illumination wavelengths (365, 385, 395, 405, 415, 808 nm), different illumination power densities, different dwell times for the photosensitive compounds on the hair, and different exposure times. The experimental setup is shown in FIG. 10 and includes heat sink 143 that is attached a a LED array 161 that is followed by a collimating lens 162 (LED array 161 and collimating lens 162 are collectively denoted radiation source 144) and mask 142. Light from the LED array 161 is collimated by collimating lens 162 and pass through apertures in mask 142 to selectively brighten hair 30.

The power densities were measured with an Ophir power meter, and the spectrum was measured with an Ocean Optics spectrometer. Each time a group of hair was taken, the photosensitive compound was applied, a specific dwell time was given, and the LED array was turned on at a specific power and for a specific time duration. The brightening results were observed with a camera and with the naked eye.

With compound number 2 we got the best results in terms of the shortest required exposure time for brightening. The most effective wavelength were 385, 395, and 405 nm. With power densities of 1 W/cm2 the exposure time was 2.5 minutes for severe brightening, but additional exposure led to hair damage. The optimal power density without hair damage was 0.5 W/cm2.

Examples of the brightened hair is shown in FIG. 10. These are only preliminary results and we believe all parameters could be further optimized.

Figure 11:
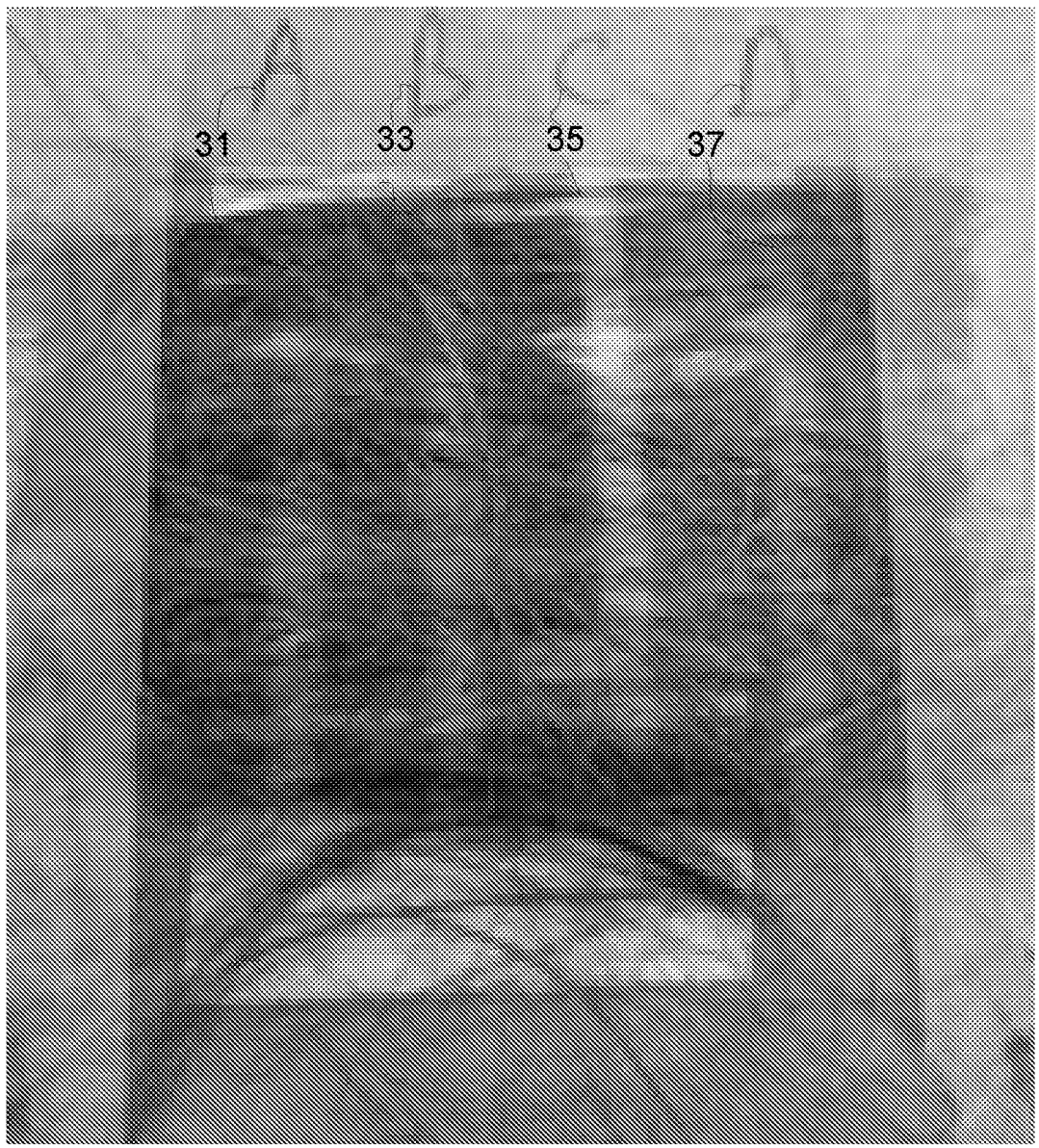
FIG. 11 is an example of brightening stripes obtained under different dwell time.

In FIG. 11 there are four brightened stripes of hair denoted A 31, B 32, C 33 and D 34.

A—obtained with a 2.5 minutes dwell time, B—obtained with 5 minutes dwell time, C— obtained with 10 minutes dwell time, D—obtained with 20 minutes dwell time. The illumination was performed at 0.5 W/cm2 through a rectangular slit. The photosensitive material was compound 4002. The wavelength was 405 nm.

FIGS. 12-17 illustrates example of hair 30, and various parts of the system 100.

Figure 12:
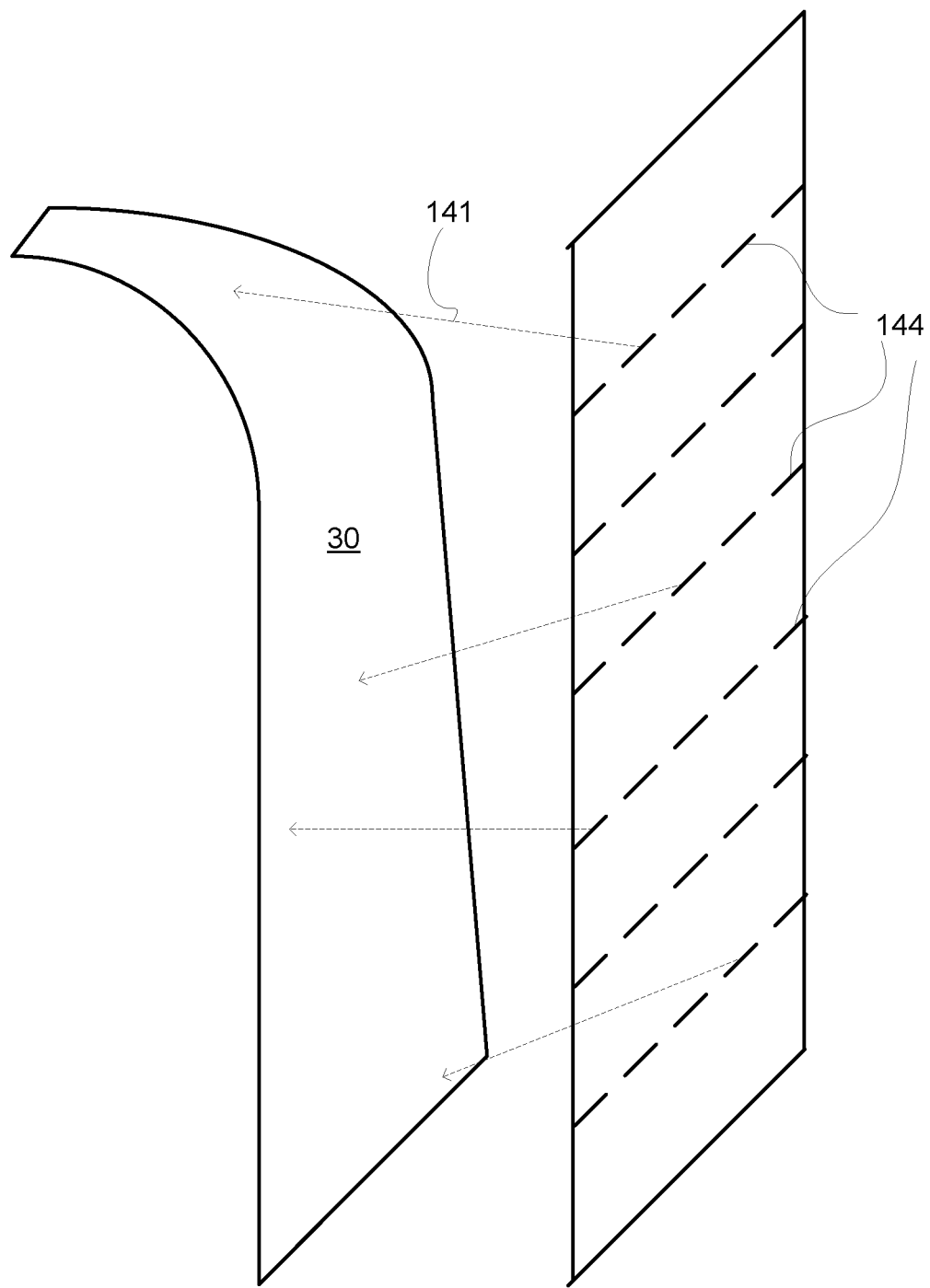
FIG. 12 is an example of hair and radiation sources.

FIG. 12 illustrates an array of radiation sources 144 that are arranged in rows and columns. The different radiation sources may be optical axes 141 that may or may not be parallel to each other.

Figure 13:
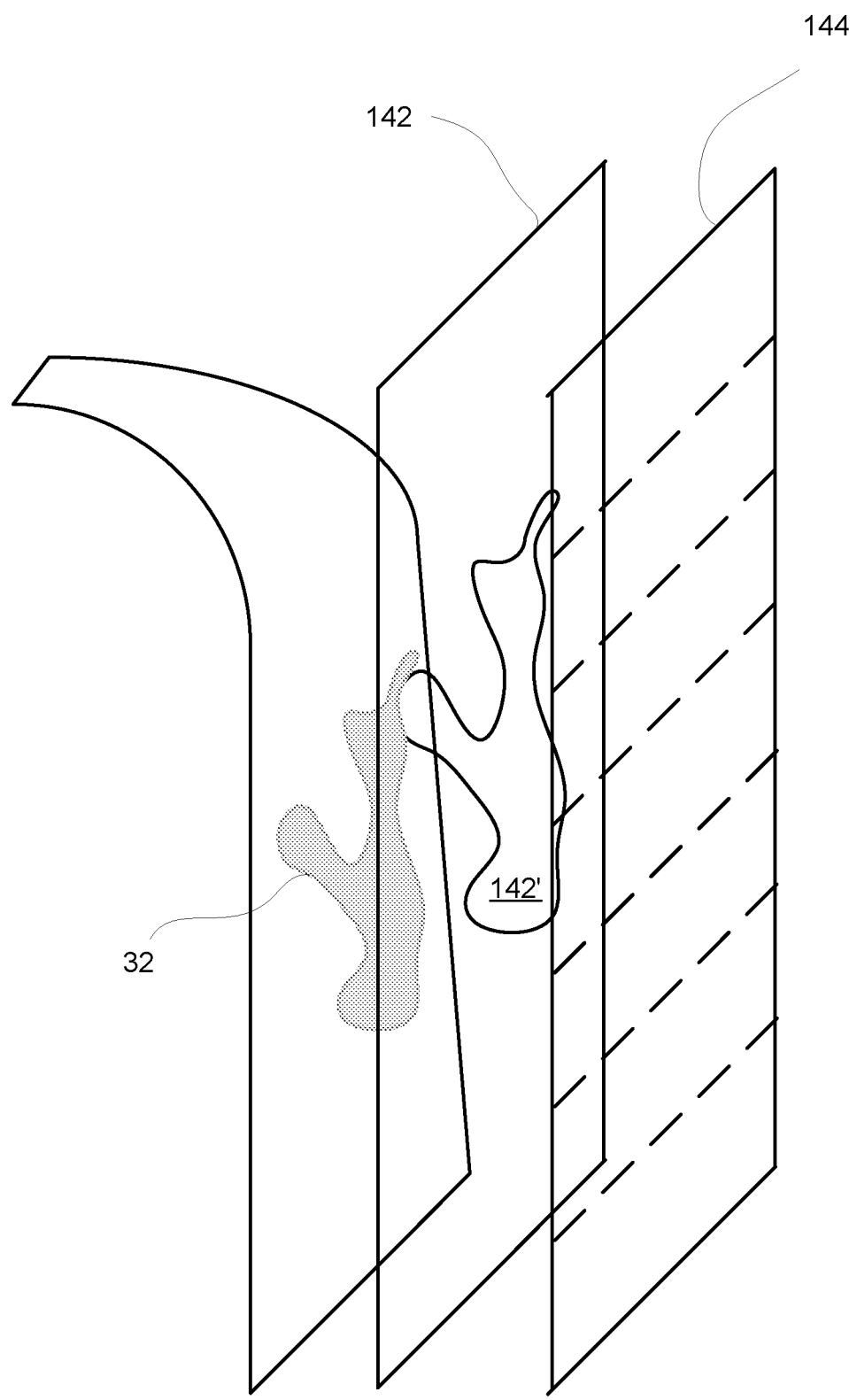
FIG. 13 is an example of hair, a mask and radiation sources.

FIG. 13 differs from FIG. 12 by illustrating a mask 142 that has a patterned aperture 142' for along radiation to pass through and form pattern 32 on hair.

Figure 14:
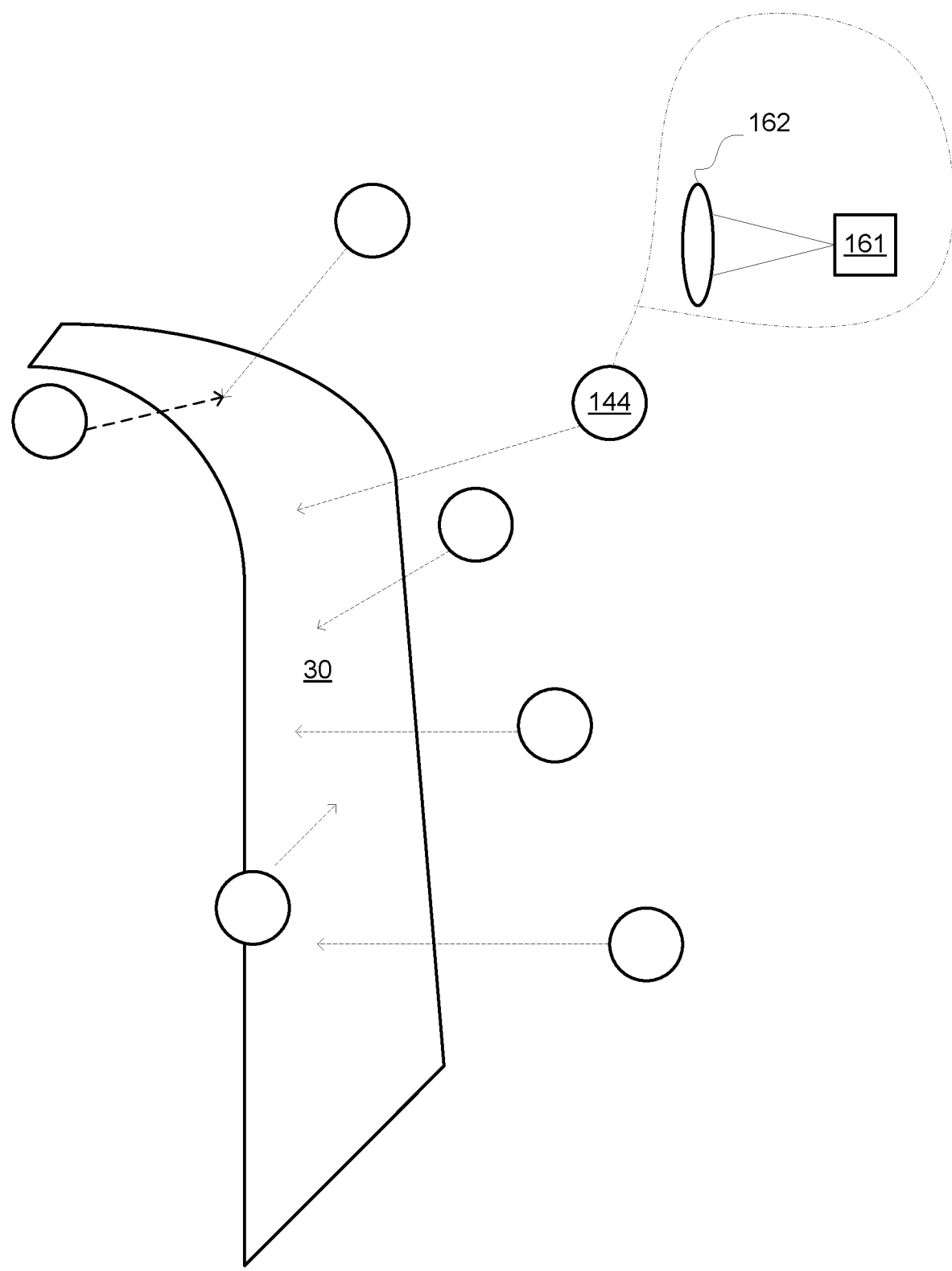
FIG. 14 is an example of hair and radiation sources.

FIG. 14 illustrates multiple spaced apart radiation sources 144—each including a radiation source 161 followed by a lens 162. The radiation sources may be lamps, LRDs, UV lamps, blue lamps and the like.

Figure 15:
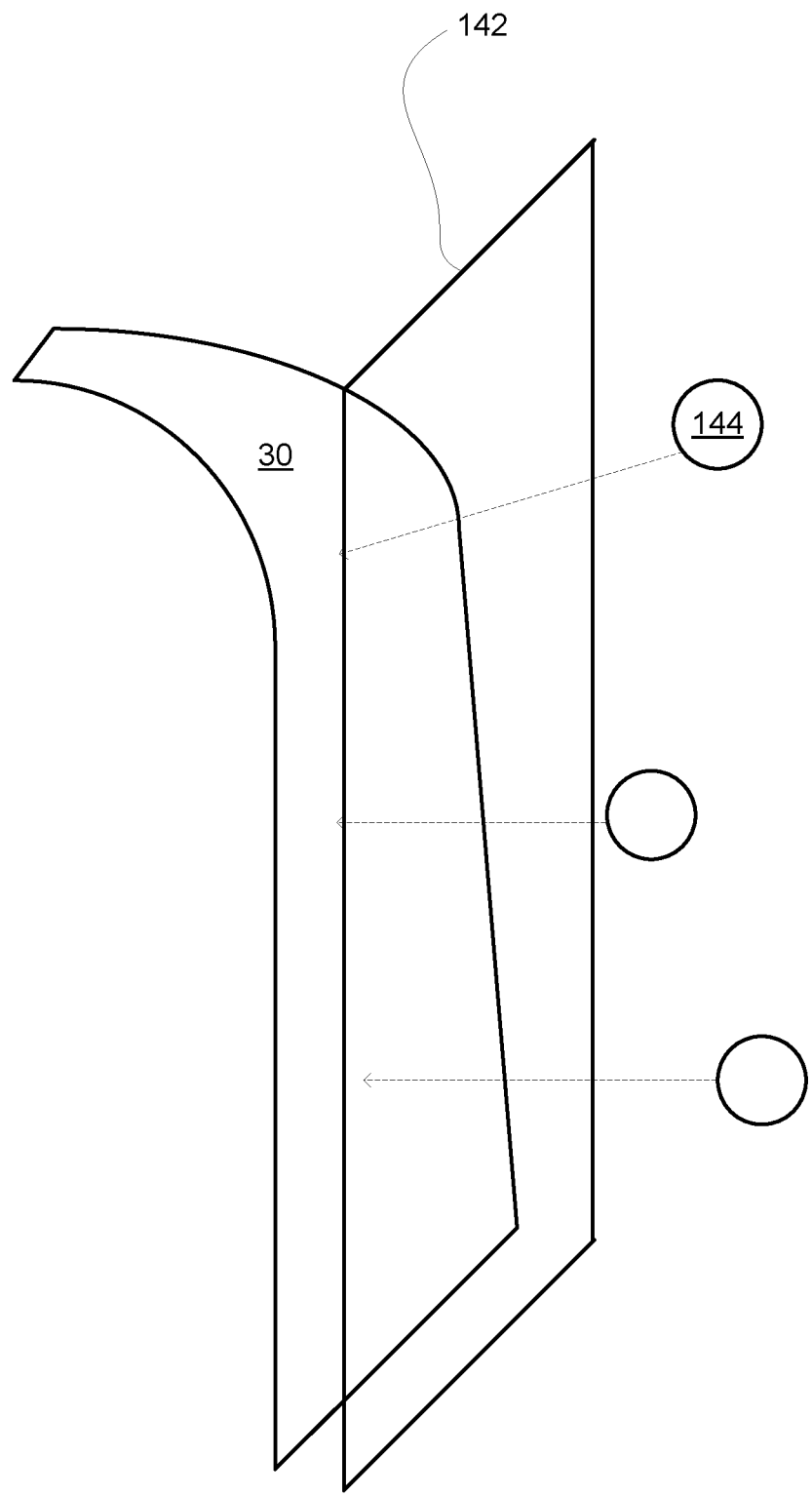
FIG. 15 is an example of hair, a mask and radiation sources.

FIG. 15 illustrates multiple spaced apart radiation sources 144 and a mask 142 positioned between the radiation sources and the hair 30.

Figure 16:
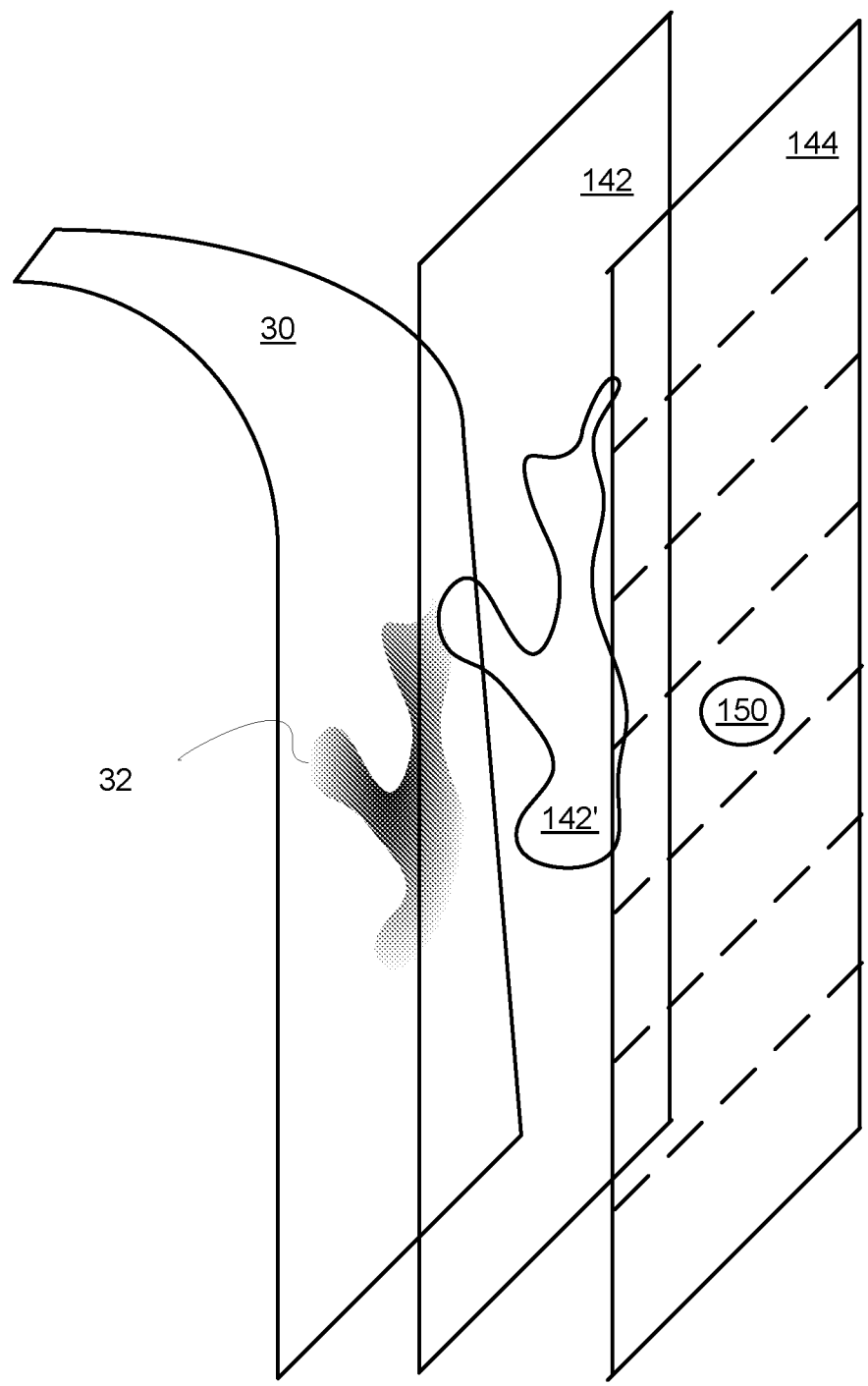
FIG. 16 is an example of hair, a mask and radiation sources.

FIG. 16 illustrates an array of radiation sources 144 that are arranged in rows and columns, a mask 142 that has a patterned aperture 142' for along radiation to pass through and form pattern 32 (in this example—of uneven brightening) on hair 30.

Figure 17:
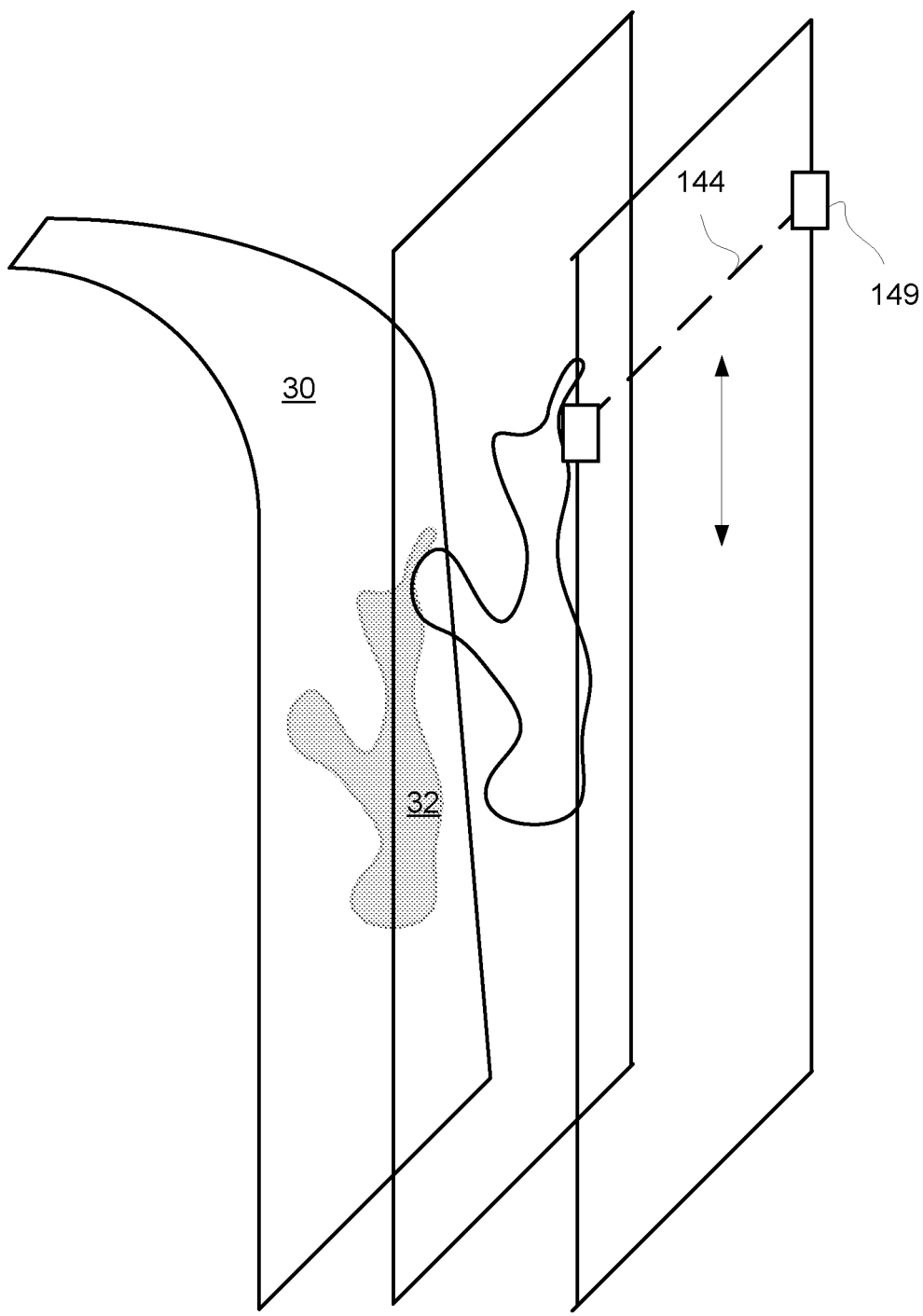
FIG. 17 is an example of hair, a mask and radiation sources.

FIG. 17 illustrates a row of radiation sources 144 that is moved by a scanning mechanism 149, a mask 142 that has a patterned aperture 142' for along radiation to pass through and form pattern 32 (in this example—of uneven brightening) on hair 30.

Figure 18:
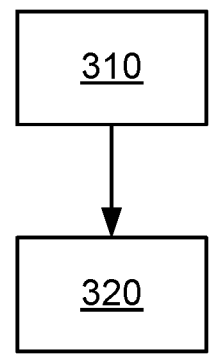
FIG. 18 is an example of a method.

FIG. 18 illustrates method 300 for selective brightening of hair, the method may include steps 310 and 320.

Step 310 may include applying at least one photosensitive material to the hair.

Step 320 may include forming at least one pattern of brightened hair by illuminating the hair by at least one pattern of illumination. The at least one pattern may cover the entire hear, or only one or more parts of the hair.

The forming of the at least one pattern may include illuminating a mask positioned between a radiation source and the hair to provide the pattern of illumination.

The illuminating may be preceded by positioning the hair between the mask and a holding element element.

The at least one of the mask and the radiation source may be proximate (for example 1-10 centimeters, less than 1 cm or more than 10 centimeters) to a back of a seat.

The mask may be a fixed mask.

The mask may be a configurable mask.

The mask may be a planar mask.

The mask may be a three dimensional mask.

The forming of the at least one pattern may include scanning at least one radiation beam to provide the at least one pattern of brightened hair.

The forming of the at least one pattern may include illuminating the hair from multiple directions by multiple radiation sources.

The forming of the at least one pattern may include illuminating the hair from multiple directions by multiple independently controllable radiation sources.

The forming of the at least one pattern may include illuminating the hair from multiple directions by at least one radiation source located within a helmet.

The forming of the at least one pattern may include forming a pattern of nonuniform brightness.

The forming of the at least one pattern may include forming a pattern of a uniform brightness.

The radiation may have a wavelength that ranges between 365 and 435 nanometer.

The radiation may have a wavelength that ranges between 400 and 435 nanometer.

The radiation may have a power density that does not exceeds Watt/cm.

The forming of the at least one pattern may include monitoring the hair and determining when to stop the illuminating based on a result of the monitoring.

The forming of the at least one pattern may include illuminating the hair from multiple directions by one or more light emitting diodes.

The forming of the at least one pattern may include illuminating the hair from multiple directions by one or more ultraviolet lamps.

The forming of the at least one pattern may include illuminating the hair from multiple directions by one or more blue lamps.

The method may include inspecting the hair before the forming of the at least one pattern; and determining at least one illumination parameter based on an outcome of the inspecting and one or more properties of the at least one pattern.

The applying of the at least one photosensitive material may include applying a mixture or solution that may include at least a majority of water, Hydrogen Peroxide, Cetyl Alcohol, Behentrimonium chloride, polyquatemium, panthenol, *Aloe vera* extract, *Camellia sinesis*, isopropyl myristate, niacinamid, fragrance, citric acid, and geraniol.

The applying of the at least one photosensitive material may include applying a mixture or solution that may include water, Hydrogen Peroxide, Cetyl Alcohol, Behentrimonium chloride, polyquatemium 10, panthenol, *Aloe vera* extract, *Camellia sinesis*, isopropyl myristate, niacinamid, fragrance, citric acid, and geraniol.

The applying of the at least one photosensitive material may include applying a mixture or solution that may include water, Hydrogen Peroxide, an emulsifier and thickening agent, an antistatic agent and conditioner, an hair body increment agent, a moisturizer and healing agent, *Aloe vera* extract, *Camellia sinesis*, a hair penetration increment agent, niacinamid, fragrance, citric acid, and geraniol.

The applying of the at least one photosensitive material may include applying a mixture or solution that may include at least a majority of Acetone Peroxide, Alcohol, Benzoic acide, Benzophenone, Benzoyl Peroxide, Benzyl, Benzylbenzoic acid, Calcium peroxide, *Calendula officinalis* flower, *Chamomilla recutita* (matricario) flower extract, Chlorine, Dimethicone peg-phosphate, Disodium edta (-), Fragrance, Glycerin, Guar Gum, Hydrogen peroxide, Hydroxyethyl cetyldimonium phosphate, *Linum usitatissimum* (linseed) seed extract, Nano Cooper powder, Nano Silver powder, *Oleo barbadensis* leaf juice, Panthenol, Polysorbate, Quaternium, Silk amino acid, Water and xanthan Gum.

The applying of the at least one photosensitive material may include applying a mixture or solution that may include at least a majority of a free peroxide, at least one of silver nanoparticles and copper nanoparticles, hair stabilizers and emulsifiers, extraction of plants, Surfactants and water.

The applying of the at least one photosensitive material may include applying a mixture or solution that may include a free peroxide, at least one of silver nanoparticles and copper nanoparticles, hair stabilizers and emulsifiers, extraction of plants, Surfactants and water.

Figure 19:
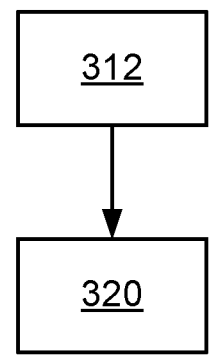
FIG. 19 is an example of a method.

FIG. 19 illustrates method 302 for selective brightening of hair, the method may include steps 312 and 320.

Step 312 may include receiving hair that may include at least one photosensitive material.

Step 320 may include forming at least one pattern of brightened hair by illuminating the hair by at least one pattern of illumination.

The forming of the at least one pattern may include illuminating a mask positioned between a radiation source and the hair to provide the pattern of illumination.

The illuminating may be preceded by positioning the hair between the mask and a holding element element.

The at least one of the mask and the radiation source may be proximate to a back of a seat.

The mask may be a fixed mask.

The mask may be a configurable mask.

The mask may be a planar mask.

The mask may be a three dimensional mask.

The forming of the at least one pattern may include scanning at least one radiation beam to provide the at least one pattern of brightened hair.

The forming of the at least one pattern may include illuminating the hair from multiple directions by multiple radiation sources.

The forming of the at least one pattern may include illuminating the hair from multiple directions by multiple independently controllable radiation sources.

The forming of the at least one pattern may include illuminating the hair from multiple directions by at least one radiation source located within a helmet.

The forming of the at least one pattern may include forming a pattern of nonuniform brightness.

The forming of the at least one pattern may include forming a pattern of a uniform brightness.

The radiation may have a wavelength that ranges between 365 and 435 nanometer.

The radiation may have a wavelength that ranges between 400 and 435 nanometer.

The radiation may have a power density that does not exceeds Watt/cm.

The forming of the at least one pattern may include monitoring the hair and determining when to stop the illuminating based on a result of the monitoring.

The forming of the at least one pattern may include illuminating the hair from multiple directions by one or more light emitting diodes.

The forming of the at least one pattern may include illuminating the hair from multiple directions by one or more ultraviolet lamps.

The forming of the at least one pattern may include illuminating the hair from multiple directions by one or more blue lamps.

The method may include inspecting the hair before the forming of the at least one pattern; and determining at least one illumination parameter based on an outcome of the inspecting and one or more properties of the at least one pattern.

The receiving may be preceded by applying a mixture or solution that may include at least a majority of water, Hydrogen Peroxide, Cetyl Alcohol, Behentrimonium chloride, polyquatemium, panthenol, *Aloe vera* extract, *Camellia sinesis*, isopropyl myristate, niacinamid, fragrance, citric acid, and geraniol.

The receiving may be preceded by applying a mixture or solution that may include water, Hydrogen Peroxide, Cetyl Alcohol, Behentrimonium chloride, polyquatemium, panthenol, *Aloe vera* extract, *Camellia sinesis*, isopropyl myristate, niacinamid, fragrance, citric acid, and geraniol.

The receiving may be preceded by applying a mixture or solution that may include water, Hydrogen Peroxide, an emulsifier and thickening agent, an antistatic agent and conditioner, an hair body increment agent, a moisturizer and healing agent, *Aloe vera* extract, *Camellia sinesis*, a hair penetration increment agent, niacinamid, fragrance, citric acid, and geraniol.

The receiving may be preceded by applying a mixture or solution that may include at least a majority of Acetone Peroxide, Alcohol, Benzoic acide, Benzophenone, Benzoyl Peroxide, Benzyl, Benzylbenzoic acid, Calcium peroxide, *Calendula officinalis* flower, *Chamomilla recutita* (matricario) flower extract, Chlorine, Dimethicone peg-phosphate, Disodium edta (-), Fragrance, Glycerin, Guar Gum, Hydrogen peroxide, Hydroxyethyl cetyldimonium phosphate, *Linum usitatissimum* (linseed) seed extract, Nano Cooper powder, Nano Silver powder, *Oleo barbadensis* leaf juice, Panthenol, Polysorbate, Quaternium, Silk amino acid, Water and xanthan Gum.

The receiving may be preceded by applying a mixture or solution that may include at least a majority of a free peroxide, at least one of silver nanoparticles and copper nanoparticles, hair stabilizers and emulsifiers, extraction of plants, Surfactants and water.

The receiving may be preceded by applying a mixture or solution that may include a free peroxide, at least one of silver nanoparticles and copper nanoparticles, hair stabilizers and emulsifiers, extraction of plants, Surfactants and water.

In the foregoing specification, the invention has been described with reference to specific examples of embodiments of the invention. It will, however, be evident that various modifications and changes may be made therein without departing from the broader spirit and scope of the invention as set forth in the appended claims.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

However, other modifications, variations and alternatives are also possible. The specifications and drawings are, accordingly, to be regarded in an illustrative rather than in a restrictive sense.

The phrase "may be X" indicates that condition X may be fulfilled. This phrase also suggests that condition X may not be fulfilled. For example—any reference to a system as including a certain component should also cover the scenario in which the system does not include the certain component. For example—any reference to a method as including a certain step should also cover the scenario in which the method does not include the certain component. Yet for another example—any reference to a system that is configured to perform a certain operation should also cover the scenario in which the system is not configured to perform the certain operation.

The terms "including", "comprising", "having", "consisting" and "consisting essentially of" are used in an interchangeable manner. For example—any method may include at least the steps included in the figures and/or in the specification, only the steps included in the figures and/or the specification.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

In the foregoing specification, the invention has been described with reference to specific examples of embodiments of the invention. It will, however, be evident that various modifications and changes may be made therein without departing from the broader spirit and scope of the invention as set forth in the appended claims.

Also, the invention is not limited to physical devices or units implemented in non-programmable hardware but can also be applied in programmable devices or units able to perform the desired device functions by operating in accordance with suitable program code, such as mainframes, minicomputers, servers, workstations, personal computers, notepads, personal digital assistants, electronic games, automotive and other embedded systems, cell phones and various other wireless devices, commonly denoted in this application as 'computer systems'.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one as or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements the mere fact that certain measures are recited in mutually different claims does not indicate that a combination of these measures cannot be used to advantage.

Any system, referred to this patent application includes at least one hardware component.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A method for selective brightening of hair, the method comprises:
   applying at least one photosensitive material to the hair; and
   forming at least one pattern of brightened hair by illuminating the hair from multiple directions and by at least one pattern of illumination, the at least one pattern of illumination is formed by multiple independently controllable radiation sources.

2. The method according to claim 1 wherein the applying of the at least one photosensitive material comprises applying a mixture or solution that comprises at least a majority of water, Hydrogen Peroxide, Cetyl Alcohol, Behentrimonium chloride, polyquatemium 10, panthenol, *Aloe vera* extract, *Camellia sinesis*, isopropyl myristate, niacinamid, fragrance, citric acid, and geraniol.

3. The method according to claim 1 wherein the applying of the at least one photosensitive material comprises applying a mixture or solution that comprises water, Hydrogen Peroxide, Cetyl Alcohol, Behentrimonium chloride, polyquatemium 10, panthenol, *Aloe vera* extract, *Camellia sinesis*, isopropyl myristate, niacinamid, fragrance, citric acid, and geraniol.

4. The method according to claim 1 wherein the applying of the at least one photosensitive material comprises applying a mixture or solution that comprises water, Hydrogen Peroxide, an emulsifier, thickening agent, an antistatic agent, a conditioner, an hair body increment agent, a moisturizer, a healing agent, *Aloe vera* extract, *Camellia sinesis*, a hair penetration increment agent, niacinamid, fragrance, citric acid, and geraniol.

5. The method according to claim 1 wherein the applying of the at least one photosensitive material comprises applying a mixture or solution that comprises at least a majority of Acetone Peroxide, Alcohol, Benzoic acide, Benzophenone, Benzoyl Peroxide, Benzyl, Benzylbenzoic acid, Calcium peroxide, *Calendula officinalis* flower, *Chamomilla recutita* (matricario) flower extract, Chlorine, Dimethicone peg-7 phosphate, Disodium edta (235-228), Fragrance, Glycerin, Guar Gum, Hydrogen peroxide, Hydroxyethyl cetyldimonium phosphate, *Linum usitatissimum* (linseed) seed extract, Nano Cooper powder, Nano Silver powder, *Oleo barbadensis* leaf juice, Panthenol, Polysorbate 20, Quaternium 80, Silk amino acid, Water and xanthan Gum.

6. The method according to claim 1 wherein the applying of the at least one photosensitive material comprises applying a mixture or solution that comprises at least a majority of a free peroxide, at least one of silver nanoparticles, copper nanoparticles, hair stabilizers and emulsifiers, extraction of plants, Surfactants and water.

7. The method according to claim 1 wherein the applying of the at least one photosensitive material comprises applying a mixture or solution that comprises a free peroxide, at least one of silver nanoparticles and copper nanoparticles, hair stabilizers and emulsifiers, extraction of plants, Surfactants and water.

8. A system comprising:
   a holding element for holding hair; and
   pattern forming elements that are configured to form at least one pattern of brightened hair by illuminating at least one photosensitive material applied to the hair by at least one pattern of illumination; wherein the pattern forming elements comprise multiple independently controllable radiation sources that are configured to form the at least one pattern by illuminating the hair from multiple directions.

9. The system according to claim 8 wherein the system is configured to form the at least one pattern comprises illuminating a mask positioned between a radiation source and the hair to provide the pattern of illumination.

10. The system according to claim 9 wherein the illuminating is preceded by positioning the hair between the mask and a holding element.

11. The system according to claim 10 wherein at least one of the mask and the radiation source are proximate to a back of a seat.

12. The system according to claim 9 wherein the mask is a fixed mask.

13. The system according to claim 9 wherein the mask is a configurable mask.

14. The system according to claim 9 wherein the mask is a planar mask.

15. The system according to claim 9 wherein the mask is a three dimensional mask.

16. A system comprising: a holding element for holding hair; and pattern forming elements that are configured to form at least one pattern of brightened hair by illuminating at least one photosensitive material applied to the hair by at least one pattern of illumination; wherein the pattern forming elements comprises a helmet that comprises at least one illumination source that is configured to form the at least one pattern by illuminating the hair from multiple directions.

17. The system according to claim 8 wherein the system is configured to form the at least one pattern by forming a pattern of nonuniform brightness.

18. The system according to claim 8 wherein the system is configured to form the at least one pattern by forming a pattern of a uniform brightness.

19. The system according to claim 8 wherein the radiation has a wavelength that ranges between 365 and 430 nanometer.

20. The system according to claim 8 wherein the radiation has a wavelength that ranges between 400 and 430 nanometer.

21. The system according to claim 8 wherein the radiation has a power density that does not exceeds 2 Watt/cm$^2$.

22. The system according to claim 8 wherein the system comprises a monitor that is configured to monitor the hair and determine when to stop the illuminating based on a result of the monitoring.

23. The system according to claim 8 wherein the multiple independently controllable radiation sources comprise one or more light emitting diodes.

24. The system according to claim 8 wherein the multiple independently controllable radiation sources comprise one or more ultraviolet lamps that are configured to illuminate the hair from the multiple directions.

25. The system according to claim 8 wherein the multiple independently controllable radiation sources comprise one or more blue lamps that are configured to illuminate the hair from the multiple directions.

26. The system according to claim 8 that is configured to inspect the hair before the forming of the at least one pattern; and when a controller of the system is configured to determine at least one illumination parameter based on an outcome of the inspecting and one or more properties of the at least one pattern.

27. A non-transitory computer readable medium that stores instructions for:
   receiving hair that comprises at least one photosensitive material; and
   forming at least one pattern of brightened hair by illuminating the hair from multiple directions and by at least one pattern of illumination, the at least one pattern of illumination is formed by multiple independently controllable radiation sources.

* * * * *